United States Patent [19]
Stein

[11] Patent Number: 6,047,720
[45] Date of Patent: Apr. 11, 2000

[54] AUTOMATIC AIR-VENT VALVE FOR HYDRAULIC SYSTEMS

[75] Inventor: Joachim Stein, Weinheim, Germany

[73] Assignee: ASG Luftfahrttechnik und Sensorik GmbH, Weinheim, Germany

[21] Appl. No.: 08/981,821

[22] PCT Filed: Jul. 19, 1996

[86] PCT No.: PCT/EP96/03186

§ 371 Date: Jun. 19, 1998

§ 102(e) Date: Jun. 19, 1998

[87] PCT Pub. No.: WO97/05415

PCT Pub. Date: Feb. 13, 1997

[30] Foreign Application Priority Data

Jul. 28, 1995 [DE] Germany .......................... 195 27 666

[51] Int. Cl.[7] .................................................. F16K 24/04
[52] U.S. Cl. ........................................... 137/199; 250/903
[58] Field of Search ............................... 137/199; 250/903

[56] References Cited

U.S. PATENT DOCUMENTS 5,211,200  5/1993  Cassidy ..................................... 137/199
5,278,426  1/1994  Barbier ................................. 250/903 X

OTHER PUBLICATIONS

Patent Abstracts of Japan, vol. 7, No. 291, Dec. 1983.

Saubere Hydraulik, Nov. 1991, pp. 24–26, and English language Abstract.

*Primary Examiner*—Gerald A. Michalsky
*Attorney, Agent, or Firm*—Dennison, Scheiner, Schultz & Wakeman

[57] ABSTRACT

A bleeder valve comprising a housing including a sensor device of material which is optically denser than gas arranged between a light transmitter and a photo-electric receiver, at least one external surface of the sensor device being disposed in a space to which gas or hydraulic fluid is admitted; when gas is in contact with the external surface, light reaches the receiver and when hydraulic fluid is in contact with the surface, light does not reach the receiver, an output signal is generated by the receiver which causes a magnetic valve to open until gas is exhausted.

9 Claims, 1 Drawing Sheet

AUTOMATIC AIR-VENT VALVE FOR HYDRAULIC SYSTEMS

BACKGROUND OF THE INVENTION

The invention relates to a venting system for hydraulic systems.

A bleeder valve for venting gases from a hydraulic system is already known. The bleeder valve has a valve body with two valve chambers, which are connected with each other by a bore, one of which has a narrowed inlet connected with the hollow chamber of the hydraulic system, and a valve seat with a first ball as the valve body assigned to the bore. A valve body is located in the first valve chamber, which is pushed away from the valve seat by its own weight and has a greater inherent weight than the hydraulic liquid. The second valve chamber contains a valve seat assigned to the bore with a second ball, prestressed by a spring, as the valve body, and has an opening towards the outside air. When the pressure in the system exceeds a predetermined value, the second ball is raised so that the air escapes (DE 92 12 977 A1).

It is furthermore known to detect impurities in hydraulic systems by means of an optical sensor (DE Mag.: "fluid", November 1991, pp. 24 to 26).

Finally, it is known to employ a light source and a light receiver for detecting gas (DE 29 05 079 A1).

Because of the separation of gasses dissolved in the liquid or because of leakage, gases can collect in some places in hydraulic systems, which possibly constitute an obstacle for operating the devices which are part of the system or for their way of functioning. Care is taken for this reason that no large air or gas volumes can form in certain locations, or respectively can increase to a size which interferes with the operation of the system. Bleeder valves can be installed at the locations in a system where such gases can collect which, when the gas volume has reached a defined size, open a conduit to a space into which the gas can escape. In most cases the bleeder valves open to the outside air. With a bleeder valve open, the hydraulic liquid displaces the gas. In this case it is necessary to prevent the hydraulic liquid, which is under pressure, from escaping through the open bleeder valve.

OBJECT OF THE INVENTION

The invention is based on the object of developing a bleeder valve for hydraulic systems, which reacts to gas by opening an outlet conduit and to fluid by closing the outlet conduit, and only reacts to gas by opening the outlet conduit if it is in a functioning state.

SUMMARY OF THE INVENTION

In accordance with the invention, this object is attained in connection with a bleeder valve for hydraulic systems in that an optical conductor, made of an optically denser material than gas, is arranged between a light transmitter and a photo-electric receiver, and is arranged with at least one exterior surface in the hollow chamber which can be charged with gas or liquid in such a way that, with gas at the exterior surface, light can reach the receiver, and with liquid at the exterior surface, no light can reach the receiver, and that the receiver generates an output signal when receiving light, which brings a magnetic valve, which is arranged in an outlet conduit between the hollow chamber, in which the fiber-optical wave guide is located, and an outer chamber, into the opening position. The bleeder valve in accordance with the invention opens the outlet conduit if all components operate correctly. If a component is faulty or has broken down, the bleeder valve does not open. For this reason it is not possible that liquid from the hydraulic system or the hydraulic device can penetrate to the outside in case of an interruption or an error in the bleeder valve.

In a preferred embodiment the optical conductor is a prism, wherein light from the light transmitter is fed into its base, and whose base the photo-electric receiver adjoins, while the top surfaces of the prism are facing the hollow chamber with the liquid, or respectively the gas. When gas surrounds the top surface of the prism, because of its total reflection in the prism the light of the light transmitter reaches the receiver, which thereupon brings the magnetic valve into the opening position. If there is liquid on the top surfaces, light from the prism goes out into the liquid, so that no light reaches the receiver. In the latter case the magnetic valve is closed. If the light transmitter or the optical receiver, or one of the components connected downstream of the light receiver or one connected downstream of the light receiver is filled, the magnetic valve will not receive a control signal for opening, even if gas is present at the prism.

Advantageous embodiments of the invention are recited in the dependent claims.

An automatic bleeder valve of the above described type is preferably attached to the top of a hydraulic liquid reservoir containing a liquid supply for a hydraulic system.

DETAILED DESCRIPTION OF THE INVENTION

Figure 1:
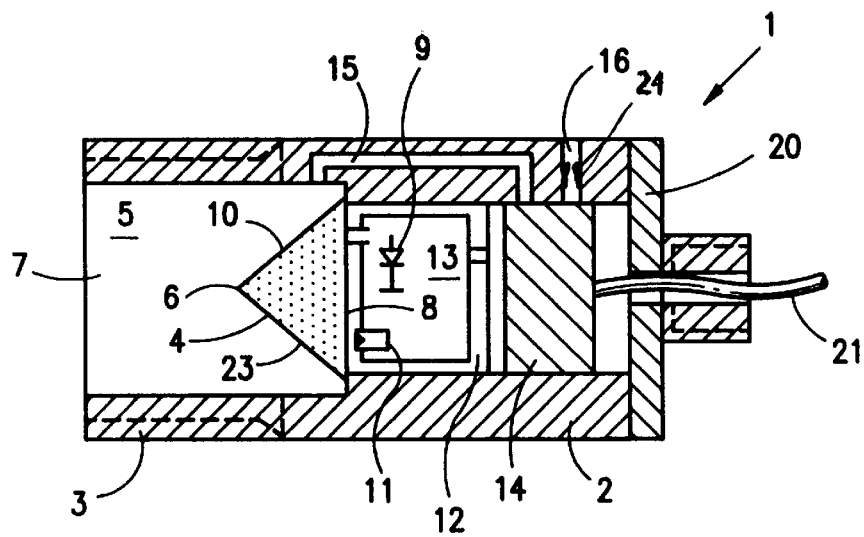
FIG. 1, an automatically operating bleeder valve in a schematic representation, partially in section.

This invention will be described in detail by means of the exemplary embodiment shown in the drawings.

A bleeder valve 1 contains a cylindrical housing 2, which is provided with an exterior thread 3 at one end. A prism 4 of a transparent material, for example glass or plastic, i.e. a material with a higher optical density than gas, is located as a light conductor in the interior of the housing 2. The prism 4 has been attached at the end of a cube-shaped hollow chamber 5 and faces the opening 7 of the cube-shaped hollow chamber 5 with its tip 6. On one side, the base 8 of the prism 4 is acted upon by light from a light transmitter 9, which can be a light-emitting diode, for example light is fed via an optical device into the base 8 into an area outside the center of the prism 4, so that the light entering the prism 4 impinges upon the top surface 10 of the prism 4. The optical device, not represented in detail, for example a lens arranged in front of the light-emitting diode, bundles the transmitted light.

A photo-electric receiver 11, which can be a light-sensitive diode, is arranged symmetrically with the center of the base 8 in relation to the light transmitter 9. The light transmitter 9 and receiver 11 are parts of a circuit 13 arranged in a hollow chamber venting in the housing 2. A magnetic valve 14, only schematically indicated, is also arranged in the hollow chamber 12 next to the circuit 13. An outlet conduit 15 in the wall of the housing 2 leads from the hollow chamber 5 to the magnetic valve 14. Furthermore, an outlet conduit 16 leads radially outward from the magnetic valve 14. The outlet conduit 16 is open to the outside.

Figure 2:
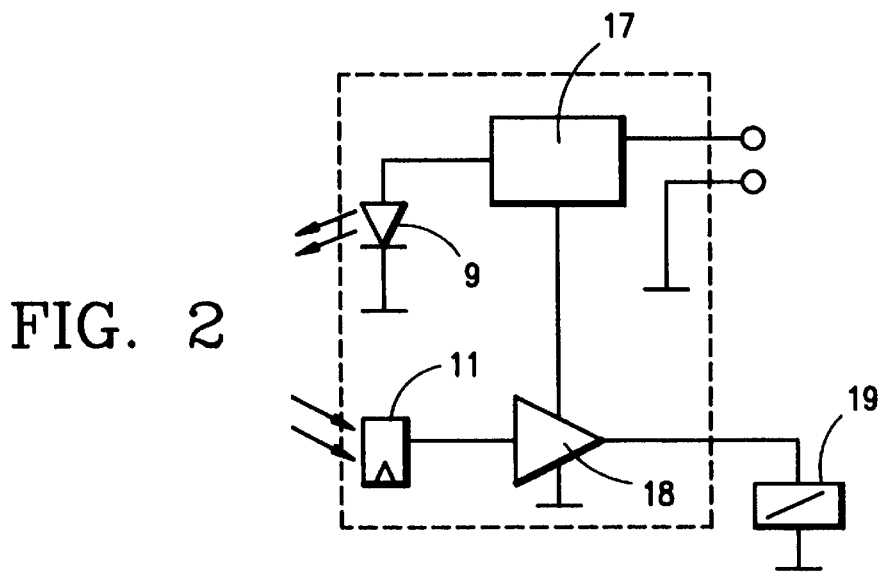
FIG. 2, a circuit diagram with details of a circuit arranged in a bleeder valve in accordance with FIG. 1, and FIG. 3, a reservoir for a hydraulic system with an automatic bleeder valve in a lateral view.
Figure 3:
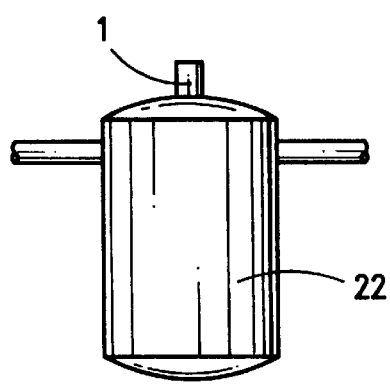

The circuit 13 is shown in greater detail in FIG. 2. It contains a power supply element 17 which provides the light transmitter 9 with voltage, if required controlled voltage. A modulating device can be connected downstream of the power supply element 17 and pulse-modulates the supply voltage for the optical receiver.

An amplifier 18 is connected downstream of the receiver 11 and can be connected with a filter for receiving pulse-modulated light. The operating voltage for the amplifier 18 is generated by the power supply element 17. The output of the amplifier 18 is connected to the coil 19 of the magnetic valve 14. The power supply element 17 is supplied with voltage through a cable 21 inserted into a front face 20 of the housing 2.

The bleeder valve 1 is arranged at a location of a hydraulic system. In particular, the bleeder valve 1 is disposed on the top of a container 22 constituting a reservoir for a hydraulic liquid. When the fluid circuit is completely filled with hydraulic liquid, the top surfaces 10, 23 of the prism 4 are in the hydraulic liquid. Therefore the light beam impinging on the top surface 10 is only slightly diffracted and leaves the prism 4 at least at the top surface 23, i.e. the receiver 11 is not acted upon by light. This means that the amplifier 18 does not transmit a control signal to the coil 19, so that the magnetic valve 14 remains closed.

If air collects in the hollow chamber 5, which displaces the liquid at the top surfaces 10, 23, the light beam transmitted by the light transmitter 9 is totally reflected at the top surfaces 10, 23 and reaches the photo-electric receiver 11, whose output signal acts on the coil 19 via the amplifier 18. Because of this, the magnetic valve 14 is opened, so that the air in the hollow chamber 5 flows through the conduit 15 via the opened magnetic valve 4 and the conduit 16 to the outside. With the magnetic valve open, the liquid flowing into the chamber 5 displaces the air and reaches the top surfaces 10, 23, which form a 90° angle. Therefore the lightbeam is refracted at the top surfaces 10, 23 in such a way that it no longer reaches the receiver. The magnetic valve 14 is therefore closed again.

The magnetic valve 1 is only opened if the components of the chain of power supply element 17, light transmitter 9, receiver 11, amplifier 8 and coil 19 operate perfectly. If a component breaks down, the coil 19 no longer receives a voltage. This also applies if one of the lines for the power supply of the electrical components is interrupted.

An interference with the optical beam sequence, for example caused by cracks in the prism or impairments of the state of the optical components, prevents the triggering of the magnetic valve 14. It is assured in this way that no fluid reaches the outside, for example the atmosphere, by damage to or interruptions of the bleeder valve 1.

A nozzle 24, which affects the air flow, is arranged in the conduit 16. In case of an unlikely hangup of the magnetic valve in the open position after the control signal from the coil 19 has been switched off, the loss of liquid is reduced to a minimum by the nozzle. It is also possible to monitor the conduit 16, for example photo-electrically, whether air or liquid is present therein. If liquid is detected, an alarm can be generated, so that the trouble source can be removed.

What is claimed is:

1. A bleeder valve arranged on top of a reservoir for a hydraulic liquid comprising:

a housing having a hollow chamber closed on one end with an end plate;

an optical conductor in the form of a prism having a base and two top surfaces, said optical conductor made of material denser than gas;

a light transmitter feeding light into the base;

a photo-electric receiver;

said light transmitter and photo-electric receiver being arranged symmetrically with a center of the base and forming a circuit within the hollow chamber;

a magnetic valve arranged between the circuit and the end plate;

said top surfaces of the optical conductor being exposed to one of gas and liquid filling the hollow chamber;

said photo-electric receiver generating an output signal when receiving light from said light transmitter; and said photo-electric receiver being exposed to light only when the hollow housing is filled with gas.

2. The bleeder valve according to claim 1, wherein the housing includes a conduit and outlet, the magnetic valve operating in response to the output signal to open the outlet and thus to bleed the gas.

3. The bleeder valve according to claim 2, wherein a nozzle is disposed at an end of the outlet.

4. The bleeder valve according to claim 2, wherein the gas is exhausted through the outlet, the hollow chamber is filled with fluid, no light is received by the photo-electric receiver and the magnetic valve operates to close the outlet.

5. A bleeder valve for hydraulic systems wherein a sensor device is arranged in a hollow chamber which can be charged with gas or liquid and where the presence of gas directs a magnetic valve into an open position, said bleeder valve comprising:

a housing which includes a hollow chamber;

an outer chamber in which a magnetic valve is arranged;

an outlet conduit in a wall of the housing which leads from the hollow chamber to the magnetic valve;

said sensor device being an optical sensor of optical conductor material being optically denser than gas; the sensor device being arranged between a light transmitter and a photo-electric receiver; said sensor device having at least one exterior surface in the hollow chamber so that with gas in said hollow chamber and thus at said exterior surface, light reaches the receiver, whereas with liquid at the exterior surface, light does not reach the receiver; said receiver generating an output signal when receiving light, said output signal directing the magnetic valve into the open position.

6. The bleeder valve in accordance with claim 5, wherein the optical conductor is a prism with a base and top surfaces, the light from the light transmitter is fed into said base and the receiver adjoins the base, the top surfaces of the prism are exterior surfaces facing the hollow chamber charged with the fluid or the gas.

7. The bleeder valve in accordance with claim 6, wherein the exterior surfaces form a 90° angle.

8. The bleeder valve in accordance with claim 5, wherein the valve housing has an outlet and a nozzle is disposed in said outlet.

9. The bleeder valve in accordance with claim 5, wherein said bleeder valve is arranged on the top of a reservoir for a hydraulic fluid.

* * * * *